(12) United States Patent
McCafferty

(10) Patent No.: US 9,962,256 B2
(45) Date of Patent: May 8, 2018

(54) BUTTRESSED HAPTIC

(71) Applicant: The Arizona Board of Regents on behalf of the University of Arizona, Tucson, AZ (US)

(72) Inventor: Sean J. McCafferty, Tucson, AZ (US)

(73) Assignee: The Arizona Board of Regents on behalf of the University of Arizona, Tucson, AZ (US)

( * ) Notice: Subject to any disclaimer, the term of this patent is extended or adjusted under 35 U.S.C. 154(b) by 0 days. days.

(21) Appl. No.: 14/421,731

(22) PCT Filed: Aug. 15, 2013

(86) PCT No.: PCT/US2013/055093
§ 371 (c)(1),
(2) Date: Feb. 13, 2015

(87) PCT Pub. No.: WO2014/028707
PCT Pub. Date: Feb. 20, 2014

(65) Prior Publication Data
US 2015/0202040 A1 Jul. 23, 2015

Related U.S. Application Data

(60) Provisional application No. 61/742,624, filed on Aug. 15, 2012.

(51) Int. Cl.
*A61F 2/16* (2006.01)

(52) U.S. Cl.
CPC .............. *A61F 2/16* (2013.01); *A61F 2/1624* (2013.01); *A61F 2/1635* (2013.01);
(Continued)

(58) Field of Classification Search
CPC .... A61F 2/1635; A61F 2/1648; A61F 2/1613; A61F 2/1629; A61F 2/1624;
(Continued)

(56) References Cited

U.S. PATENT DOCUMENTS 7,621,949 B2    11/2009   Deacon et al.
7,976,520 B2    7/2011    Nun
(Continued)

FOREIGN PATENT DOCUMENTS

WO    2009/015226    1/2009

OTHER PUBLICATIONS

Notification of Transmittal of the International Search Report and the Written Opinion of the International Searching Authority, or the Declaration for Int'l Application No. PCT/US2013/055093 dated Nov. 12, 2013, 12 pages.

*Primary Examiner* — David H Willse
*Assistant Examiner* — Tiffany Shipmon
(74) *Attorney, Agent, or Firm* — Barry L. Davison; Davis Wright Tremaine LLP

(57) ABSTRACT

A haptic supporting an intraocular lens (IOL) in the eye permits radial tension from ciliary muscle relaxation rather than contraction to alter the lens power. The IOL is supported by the overlying tissue in the eye such as iris root, sclera and ciliary process, so that anterior and posterior forces on IOL are balanced, and buckling or displacement of lens in the eye or haptic is reduced or prevented. The haptic is of a thickness so as to increase stiffness and to reduce or prevent IOL buckling or displacement.

16 Claims, 1 Drawing Sheet

(52) U.S. Cl.
CPC . *A61F 2002/169* (2015.04); *A61F 2002/1681* (2013.01); *A61F 2002/1682* (2015.04); *A61F 2002/1689* (2013.01); *A61F 2210/0014* (2013.01)

(58) Field of Classification Search
CPC ...... A61F 2002/1689; A61F 2002/1682; A61F 2002/169
USPC .............................................. 623/6.37, 6.49
See application file for complete search history.

(56) References Cited

U.S. PATENT DOCUMENTS

| | | | |
|---|---|---|---|
| 2002/0138140 A1* | 9/2002 | Hanna | A61F 2/1613 623/6.37 |
| 2004/0238293 A1 | 12/2004 | Peterson et al. | |
| 2004/0238392 A1 | 12/2004 | Peterson et al. | |
| 2007/0078515 A1* | 4/2007 | Brady | A61F 2/1613 623/6.37 |
| 2008/0300680 A1 | 12/2008 | Joshua | |
| 2010/0131061 A1* | 5/2010 | Callahan | A61F 2/1613 623/6.49 |
| 2011/0313523 A1 | 12/2011 | Hayes | |

* cited by examiner

BUTTRESSED HAPTIC

BACKGROUND OF THE INVENTION

Cataract surgery has been the most common surgery in the United States for more than 30 years and its frequency is increasing. A cataract is an opacity of the eye's natural lens which is typically age related. The cataract causes progressively decreased vision along with a progressive decrease in the individual's ability to function in their daily activities. This decrease in function with time can become quite severe. Cataract surgery removes the opaque natural lens and replaces it with a synthetic and clear lens that restores the vision. Synthetic lenses have been very successful at restoring vision for a predetermined focal distance by properly sizing the lens for the individual. However, they have not been able to restore the eye's ability to accommodate.

Accommodation is the eye's ability to change the shape of its natural lens and thereby change its focal distance. This allows an individual to focus on an object at any given distance in their view with an autonomic nervous system feedback response. The person does this automatically, without thinking, by innervating their ciliary body muscle in the eye. The ciliary muscle adjusts radial tension on the natural lens and changes the lens' surface curvatures, and thus adjusts the focal distance of the eye in order that one may focus on a given object.

Without the ability to accommodate, lenses such as reading glasses must be relied upon to focus desired objects. Typically, cataract surgery will leave the individual with a fixed focal distance, usually greater than 20 feet. This allows them to function in activities such as driving without glasses. For activities such as computer work or reading, they need separate glasses.

Several attempts have been made with cataract surgery to restore accommodation in an eye that has lost its ability to change its focal distance. The most successful of these rely upon the insertion of lenses with two to three discrete focal distances. The result with these types of lenses has been only fair, since the designs compromise the overall quality of the vision in exchange for multiple focal distances. Another design alters the position of a fixed focal distance lens by ciliary muscle contraction and thereby changes the overall focal distance of the eye. This design has diminished in popularity, due to poor performance.

A previously disclosed accommodating intraocular lens invented at the University of Arizona (hereinafter "IOL") utilizes radial tension provided by relaxation of the ciliary muscle to provide an anterior vectored force on the lens thus allowing it to alter the overall lens power without the need to move its position within the eye. The obvious problem is that there must be a posterior vectored force to maintain the lens in a static position within the eye. Furthermore, since this force is tonic and variable, the counter force must be sustainable without migration in the IOL position.

In certain types of haptics, such as ones proposed in U.S. Pat. No. 7,976,520 and U.S. 2008/0300680, the haptics require anchors to puncture or penetrate into the eye wall to support the haptic and keep it in the proper location. This requires a more invasive surgery procedure, which is undesirable.

It is therefore desirable to provide a haptic for supporting the IOL so that it is accommodating and the haptic exerts a sustainable counter force that reduces or prevents migration of the IOL from its proper position, preferably without having to penetrate into eye tissue to support the haptic and keep it in the proper location.

SUMMARY OF THE INVENTION

The embodiments of the invention are directed to haptics for supporting an intraocular lens (IOL) in an eye, wherein the IOL changes its focal distance using the eye's natural mechanism of ciliary body muscle tension. Relaxation of the ciliary muscle in the eye causes an anterior force to act on the IOL, altering its focusing power.

In one embodiment of the invention, the haptic comprises a foldable sheet of material in the shape of a dome or a portion of a dome, wherein the sheet is of a size that when the sheet is inserted in the ciliary sulcus, the sheet is buttressed by overlying tissue on the anterior side to prevent the IOL from buckling or moving in the eye by the anterior force.

In another embodiment of the invention, the haptic comprises a sheet of material in the shape of a butterfly with two wing portions each having a flange, wherein the sheet has sufficient thickness and the two wing portions are each of an angular extent to allow adequate stiffness of the haptic structure as to prevent axial and rotational buckling.

In yet another embodiment of the invention, the haptic comprises a curved foldable sheet of material in the shape of a butterfly with two wing portions each having a flange, wherein when the sheet is inserted in the ciliary sulcus, the flanges of the two wing portions fit snugly into the ciliary sulcus, and wherein the haptic is kept in place in the eye substantially without migration by adhesive force between the two flanges and eye tissue in contact with the haptic, without need to anchor the haptic by penetration into eye tissue.

All patents, patent applications, articles, books, specifications, other publications, documents and things referenced herein are hereby incorporated herein by this reference in their entirety for all purposes. To the extent of any inconsistency or conflict in the definition or use of a term between any of the incorporated publications or documents and the text of the present document, the definition or use of the term in the present document shall prevail.

BRIEF DESCRIPTION OF THE DRAWINGS

Identical components in this application are labeled by the same numerals.

DETAILED DESCRIPTION OF EXEMPLARY EMBODIMENTS

Figure 1:
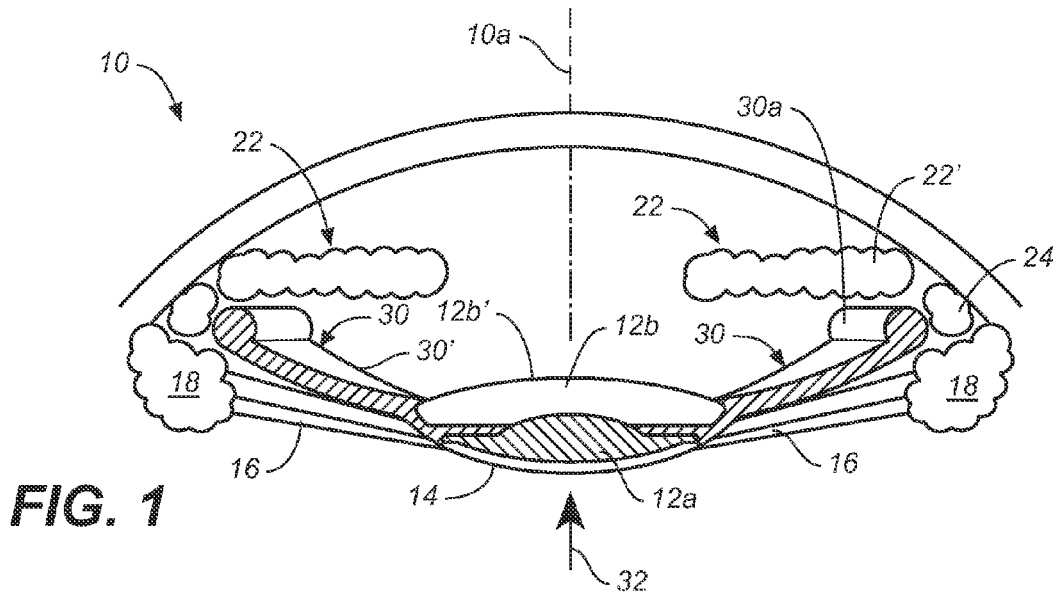
FIG. 1 is a partly cross-sectional view and partly perspective view of a haptic and an IOL supported by the haptic, and of an eye into which the haptic and IOL have been surgically inserted, to illustrate one embodiment of the invention.

FIG. 1 is a partly cross-sectional view and partly perspective view of a haptic and an IOL supported by the haptic, and of an eye into which the haptic and IOL have been surgically inserted, to illustrate one embodiment of the invention. Before this embodiment is described, it is useful to first examine the pertinent parts of the eye involved in its accommodation.

The natural lens is surrounded by an elastic capsular bag. When the natural lens is removed in cataract surgery, the anterior portion of the capsular bag is typically removed, while the remaining sides and posterior portion of the capsular bag are left in place. What is shown in FIG. 1 is therefore only the remaining sides and posterior portion of the capsular bag, labeled 14 in FIG. 1 and referred to as the "capsular bag" hereinafter. The IOL 12 has two portions 12a and 12b. The natural lens (not shown) in the eye 10 (as well as the IOL 12 that replaces the natural lens) is contained within the capsular bag 14. The lens (whether natural or IOL) together with the capsular bag are supported by zonules or zonular fibers 16 that attach to the edge or rim of the capsular bag like trampoline springs and connect the contained lens and lens capsular bag to the surrounding ciliary body 18. The zonules or zonular fibers 16 thus support and suspend the lens and lens capsular bag in the eye. The ciliary body is a ring of muscle sitting behind the iris 22, where the space between the iris root and the ciliary body is the ciliary sulcus 24. The ciliary muscle can be thought of as a camera diaphragm. When this muscle contracts, the central "hole" within the muscle gets smaller, causing the zonular fibers, which act as elastic springs, to relax their tension on the capsular bag. When this happens, the lens in the capsular bag also relaxes, and gets rounder or increases in curvature. This has the effect of reducing the focal distance to allow the eye to focus on near objects, for reading for example.

When the ciliary muscle relaxes, however, the central "hole" within the muscle gets larger, causing the zonular fibers, which act as elastic springs, to become taut and shorter. This has the effect of stretching the capsular bag, flattening the lens and thus increasing the focal distance for viewing more distant objects. The eye 10 has an axis 10a in the viewing direction of the eye. Thus, when the ciliary muscle relaxes, the zonules provide an anterior force 32 on the lens capsular bag along the axial direction 10a. The word "anterior" as used in the term "anterior force" means a direction pointing towards the front of the eye and in the viewing direction of the eye. This is also illustrated in FIG. 1 in the direction of the arrow 32. The haptic 30 permits the radial tension of the zonules to provide the anterior force on the lens to alter its power. As noted above, unless this force is countered, the lens and capsular bag will migrate in the eye, which is undesirable.

Figure 2:
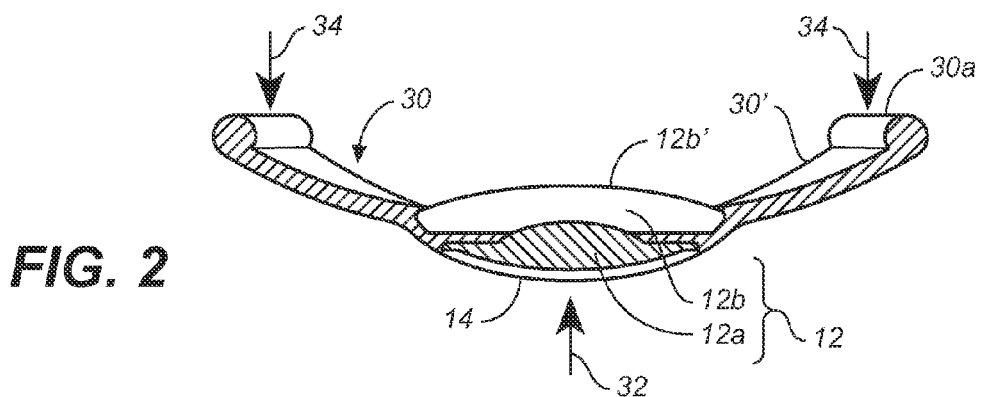
FIG. 2 is a partly cross-sectional view and partly perspective view of the haptic and IOL of FIG. 1.

In one embodiment of the invention, the haptic 30 is a curved sheet of material which forms an integral body with the lens 12 and lens capsular bag 14, and a continuous surface 30' with the anterior surface 12b' of the lens portion 12b. This is illustrated in FIGS. 1 and 2. The haptic is preferably designed as cut-out of a sphere or inverted dome and appears to be a portion of a bowl in FIG. 1. FIG. 2 is a partly cross-sectional view and partly perspective view of the haptic and IOL of FIG. 1. This inverted dome shape enables the haptic to maximally transfer the pressure or anterior force 32 applied to the posterior surface of the lens and lens capsular bag out to the anchor points of the haptic seated in the ciliary sulcus 24 of the eye. The ciliary sulcus 24 is the angular space between the root 22' of iris 22 and the ciliary body 18. The iris root, ciliary body, and overlying sclera (not shown) are the eye tissue that counters the force vector from the haptic which is directed anteriorly along axis 10a and radially outward (tangential to the sphere or dome of the haptic at the anchor point) (see FIG. 1). In other words, the iris root, ciliary body, and overlying sclera apply counter posterior forces along directions 34 to anterior force 32, by butting against flanges 30a (FIG. 2) of the haptic 30. The directions of the anterior force and of the counter posterior forces 34 are shown in FIG. 2.

The haptic design would simply buckle at the mid-position of the haptic 30 due to applied force 32 at the apex of the inverted dome shaped haptic 30 if unsupported. Therefore, the curvature of the spherical cut-out or dome is designed such that the flange 30a of haptic 30 is in continuous positional contact with the overlying tissue (iris root, ciliary body and overlying sclera). The flange design is sized for the ciliary sulcus 24 (that is, the flange 30a fits snugly into the ciliary sulcus 24) so that the flange places tension on the above mentioned overlying structures (see FIG. 1). The overlying tissue then buttresses the inverted dome shaped haptic on its anterior side, preventing it from buckling in the axial direction 10a. This in effect places the haptic under a compression force only and limits shear and bending moment. The sole compression force over a large cross-section haptic makes the structural design very stiff and able to minimize anterior displacement of the lens during actuation from the posterior applied force 32.

The ideal haptic design would be a complete dome anchored 360 degrees around the sulcus. However, this size would prevent the lens from being placed into the eye through a small incision. Therefore, the cut-out of the dome or sphere is a compromise. The haptic remains relatively thick to prevent out-of-plane buckling or rotational buckling. Also the thick haptic increases the structural stiffness. In one embodiment, the thickness of the haptic is between about 300 microns to about 1 mm thick.

Figure 3:
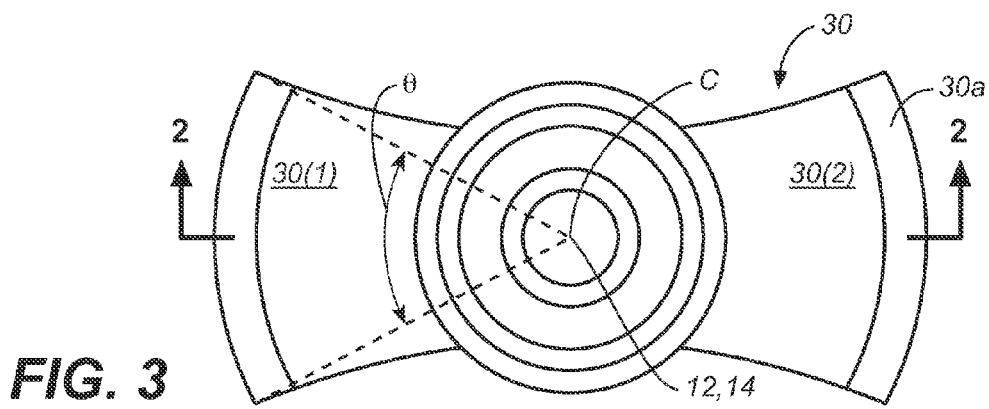
FIG. 3 is top view of the haptic and IOL to illustrate the embodiment of the invention of FIG. 1.

FIG. 3 is a top view of the haptic and IOL to illustrate one embodiment of the invention of FIG. 1. As shown in FIG. 3, the haptic has two wing portions 30(1) and 30(2), so that the haptic has an overall butterfly shape. In this embodiment, the sheet of material in the haptic 30 is of sufficient thickness and the two wing portions are each of an angular extent so as to prevent axial and rotational buckling caused by the anterior force 32 or other forces. The butterfly shaped haptic is preferably a sheet that is foldable so that it can be handled with ease during cataract surgery requiring only a small incision. The butterfly shape also reduces the amount of material and thus, the cost, required for the haptic. However, the two wing portions should be large enough to reduce rotational buckling of the haptic. In one implementation of this embodiment, the flanges 30a of the wing portions subtend an angle θ that is not less than 40 degrees at center C of the haptic and lens 12. FIG. 2 is a partly cross-sectional view along the line 2-2 of FIG. 3.

In one embodiment, the haptic 30 has flanges 30a at its outward extremities in the shape of an enlarged rounded outer rim. This flange design increases the surface contact area with the tissue in the sulcus, thereby decreasing the contact stress. Migration of foreign bodies under stress in tissue is a well-documented phenomenon.

This form of biological tissue "creep" must be prevented as the lens' actuation requires it to maintain a static position long term. The design minimizes the contact stress with the tissue and will minimize creep or migration through the tissue, so that the lens 12 remains substantially unchanged in its position when the ciliary muscle relaxes, causing the anterior force 32 to be applied to the lens. Thus, the anchoring of the haptic in the eye is by contact forces only. Even without any kind of anchoring requiring penetration into surrounding eye tissue (e.g. the sclera), the haptic stays in place with little or no migration due to the adhesive forces between the haptic and the eye tissue surrounding the ciliary sulcus in contact with the flanges 30a, despite the effect of the anterior force 32 and eye movement. The haptic 30 is kept in its desired location by the adhesive forces mentioned above, and also by the opposing natural forces (anterior force 32 and the posterior forces 34 by the overlying tissue that counter and balance the anterior force 32). Thus unlike the conventional haptics described above, there is no need for the haptic to be anchored by puncturing or penetration into the sclera or other eye tissue.

The material of the haptic 30 is biocompatible and preferably very pliable and has "memory" so that it could be folded and placed through a small incision. Materials such as acrylic or silicone would do well for this application and would not compromise the required stiffness with the "buttressed" dome design.

While the invention has been described above by reference to various embodiments, it will be understood that changes and modifications may be made without departing from the scope of the invention, which is to be defined only by the appended claims and their equivalents.

What is claimed is:

1. A haptic for supporting an intraocular lens (IOL) in an eye, wherein said IOL changes its focal distance using the eye's natural mechanism of ciliary body muscle tension, so that relaxation of the ciliary muscle in the eye causes an anterior force to act on the IOL, altering its focusing power, said haptic comprising a foldable solid sheet of material in the shape of an anterior facing inverted dome, or a portion of a dome, having an outer flange configured to fit snugly into the ciliary sulcus such that the dome curvature provides for continuous positional contact of the outer flange with overlying tissue comprising iris root, ciliary body, and overlying sclera, to provide, in response to the anterior force, a balancing posterior force, wherein said sheet has sufficient thickness to allow adequate stiffness of the haptic structure to transfer the anterior force to the posterior surface of the lens to alter its shape and power, and prevent axial and rotational buckling, and wherein said sheet is of a size that when said sheet is inserted in the ciliary sulcus, the sheet is buttressed by the overlying tissue on the anterior side to prevent the IOL from buckling or moving in the eye by the anterior force.

2. The haptic of claim 1, wherein said haptic forms an integral body with the IOL.

3. The haptic of claim 1, wherein said haptic permits radial tension exerted by zonules in the eye caused by relaxation of the ciliary muscle to provide anterior vectored force on the lens to alter the lens power.

4. The haptic of claim 1, wherein said haptic is kept in place in the eye substantially without migration by adhesive force between the haptic and eye tissue in contact with the haptic, without need to anchor the haptic by penetration into eye tissue.

5. The haptic of claim 1, wherein when the sheet is inserted in the ciliary sulcus, the sheet is buttressed by the iris root, the ciliary body and the overlying sclera of the eye to counter the anterior force exerted by the zonules when the ciliary muscle is relaxed.

6. The haptic of claim 1, wherein said sheet has a thickness of 300 microns to 1 mm.

7. The haptic of claim 1, wherein location of said IOL does not change substantially when the ciliary muscle relaxes.

8. A haptic for supporting an intraocular lens (IOL) in an eye, wherein said IOL changes its focal distance using the eye's natural mechanism of ciliary body muscle tension, so that relaxation of the ciliary muscle in the eye causes an anterior force to act on the IOL, altering its focusing power, said haptic comprising a solid sheet of material in the shape of a butterfly with two anteriorly-curving wing portions each having an outer flange configured to fit snugly into the ciliary sulcus such that the curvature provides for continuous positional contact of the outer flange with overlying tissue comprising iris root, ciliary body, and overlying sclera, to buttress the haptic and provide, in response to the anterior force, a balancing posterior force to prevent anterior/posterior dislocation of the IOL in the eye, wherein said sheet has sufficient thickness and the two wing portions are each of an angular extent to allow adequate stiffness of the haptic structure to transfer the anterior force to the posterior surface of the lens to alter its shape and power, and to prevent axial and rotational buckling.

9. The haptic of claim 8, said sheet having a thickness of 300 microns to 1 mm and each of said flanges of the two wing portions subtending an angle of not less than 40 degrees at a center of the sheet, to prevent axial and rotational buckling of the sheet caused by said anterior force.

10. The haptic of claim 8, wherein the flanges are buttressed by the overlying tissue on the anterior side to prevent the IOL from buckling or moving in the eye by the anterior force.

11. The haptic of claim 8, wherein said sheet is curved in shape and permits radial tension exerted by zonules in the eye from relaxation of the ciliary muscle to provide anterior vectored force on the lens to alter the lens power.

12. A haptic for supporting an intraocular lens (IOL) in an eye, wherein said IOL changes its focal distance using the eye's natural mechanism of ciliary body muscle tension, so that relaxation of the ciliary muscle in the eye causes an anterior force to act on the IOL, altering its focusing power, said haptic comprising a curved foldable solid sheet of material in the shape of a butterfly with two anteriorly-curving wing portions each having an outer flange, wherein when said sheet is inserted in the ciliary sulcus, said flanges of the two wing portions fit snugly into the ciliary sulcus such that the curvature provides for continuous positional contact of the outer flange with overlying tissue comprising iris root, ciliary body, and overlying sclera, to buttress the haptic and provide, in response to the anterior force, a balancing posterior force to prevent anterior/posterior dislocation of the IOL in the eye, wherein said sheet has sufficient thickness to allow adequate stiffness of the haptic structure to transfer the anterior force to the posterior surface of the lens to alter its shape and power, and prevent axial and rotational buckling, and wherein said haptic is kept in place in the eye substantially without migration by adhesive force between the two flanges and eye tissue in contact with the haptic, without need to anchor the haptic by penetration into eye tissue.

13. The haptic of claim 12, wherein said sheet is made of a biocompatible material.

14. The haptic of claim 12, wherein said sheet is made of a material that has memory.

15. The haptic of claim 12, wherein said sheet is made of a foldable biocompatible material that includes a material currently utilized for making the IOL.

16. The haptic of claim 15, wherein said sheet is made of a material that includes acrylic or silicone.

* * * * *